(12) United States Patent
Hsieh et al.

(10) Patent No.: US 10,993,973 B2
(45) Date of Patent: May 4, 2021

(54) PHARMACEUTICAL COMPOSITION AND FOOD COMPOSITION WITH STRAINS OF LACTIC ACID BACTERIA FOR IMPROVING OF KIDNEY DISEASE AND INHIBITING INFLAMMATION

(71) Applicant: Glac Biotech Co., Ltd, Tainan (TW)

(72) Inventors: Pei-Shan Hsieh, Tainan (TW); Yi-Chun Tsai, Tainan (TW); Chung-Wei Kuo, Tainan (TW); Hsieh-Hsun Ho, Tainan (TW); Hung-Chih Lin, Tainan (TW); Jiu-Yao Wang, Tainan (TW)

(73) Assignee: Glac Biotech Co., Ltd., Tainan (TW)

( * ) Notice: Subject to any disclaimer, the term of this patent is extended or adjusted under 35 U.S.C. 154(b) by 143 days.

(21) Appl. No.: 16/039,800

(22) Filed: Jul. 19, 2018

(65) Prior Publication Data

US 2019/0358273 A1 Nov. 28, 2019

(30) Foreign Application Priority Data

May 28, 2018 (TW) .................................. 107118119

(51) Int. Cl.
| | | |
|---|---|---|
| *A61K 35/745* | (2015.01) | |
| *A61K 35/747* | (2015.01) | |
| *A61P 13/12* | (2006.01) | |
| *A61L 29/00* | (2006.01) | |
| *A23L 29/00* | (2016.01) | |

(52) U.S. Cl.
CPC .......... *A61K 35/745* (2013.01); *A23L 29/065* (2016.08); *A61K 35/747* (2013.01); *A61P 13/12* (2018.01); *A23Y 2220/03* (2013.01); *A23Y 2300/25* (2013.01); *A23Y 2300/55* (2013.01)

(58) Field of Classification Search
None
See application file for complete search history.

(56) References Cited

U.S. PATENT DOCUMENTS

| | | | | |
|---|---|---|---|---|
| 7,785,635 | B1 * | 8/2010 | Boileau .................. | A23K 10/18 424/558 |
| 2005/0175598 | A1 * | 8/2005 | Boileau ................ | A61K 35/745 424/93.45 |
| 2015/0250835 | A1 * | 9/2015 | Huang ................... | A61K 45/06 424/48 |

OTHER PUBLICATIONS

NCT03228563, The Effect of Probiotics on Chronic Kidney Disease, ClinicalTrials Webpage, Jul. 25, 2017 (Year: 2017).*
Guida et al., Effect of short-term synbiotic treatment on plasma p-cresol levels in patients with chronic renal failure: A randomized clinical trial, Nutrition, Metabolism & Cardiovascular Diseases (2014) 24 1043-1049 (Year: 2014).*
Ranganathan et al., Probiotic dietary supplementation in patients with stage 3 and 4 chronic kidney disease: a 6-month pilot scale trial in Canada, Current Medical Research and Opinion, 25:8, 1919-1930 (Year: 2009).*
Khailova et al., Bifidobacterium bifidum improves intestinal integrity in a rat model of necrotizing enterocolitis, Am. J. Physiol. Gastrointest. Liver Physiol., Nov. 2009; 297(5): G940-G949 (Year: 2009).*
Marteau et al., Effect of chronic ingestion of a fermented dairy product containing Lactobacillus acidophilus and Bifidobacterium bifidum on metabolic activities of the colonic flora in humans, Am. J Clinical Nutrition, 1990;52:685-8 (Year: 1990).*
Ranganathan—2010, Pilot Study of Probiotic Dietary Supplementation for Promoting Healthy Kidney Function in Patients with Chronic Kidney Disease, Adv Ther (2010) 27(9):634-647. (Year: 2010).*
George et al., Role of prebiotic and probiotic in the management of chronic kidney disease patients, International Journal of Medical Research & Health Sciences, 2016, 5, 2:50-53 (Year: 2016).*
Koppe et al., Probiotics and chronic kidney disease, Kidney International (2015) 88, 958-966 (Year: 2015).*
Sakata et al., Unification of Bifidobacterium infantis and Bifidobacterium suis as Bifidobacterium longum, International Journal of Systematic and Evolutionary Microbiology (2002), 52, 1945-1951 (Year: 2002).*
Araya et al., "Guidelines for the Evaluation of Probiotics in Food", World Health Organization, London Ontario, Canada Apr. 30 and May 1, 2002, pp. 1-12.

* cited by examiner

*Primary Examiner* — Louise W Humphrey
*Assistant Examiner* — Srikanth Patury
(74) *Attorney, Agent, or Firm* — Muncy, Geissler, Olds & Lowe, P.C.

(57) ABSTRACT

The present invention provides a *lactobacillus* strain-containing pharmaceutical composition and food composition for improving of kidney disease and inhibiting inflammation, which comprises an isolated lactic acid bacteria strain. The isolated lactic acid bacteria strain is at least one selected from a group including BLI-02 strain, CGMCC No. 15212, *Bifidobacterium longum* subsp. *infantis*, TYCA06 strain, CGMCC No. 15210, *Lactobacillus acidophilus*, VDD088 strain, CGMCC No. 15211, *Bifidobacterium bifidum*, and combinations thereof.

16 Claims, 6 Drawing Sheets

Fig. 8

PHARMACEUTICAL COMPOSITION AND FOOD COMPOSITION WITH STRAINS OF LACTIC ACID BACTERIA FOR IMPROVING OF KIDNEY DISEASE AND INHIBITING INFLAMMATION

BACKGROUND OF THE INVENTION

1. Field of the Invention

The present invention relates to a pharmaceutical composition and food composition with strains of lactic acid bacteria, particularly to a pharmaceutical composition and food composition with strains of lactic acid bacteria both for improving kidney disease and inhibiting inflammation.

2. Description of the Prior Art

With change of dietary habit, people suffering from chronic kidney disease are growing year after year. Although the patients of initial-stage chronic kidney disease may have the symptoms of proteinuria and hematuria, instant therapy and dietary control can decelerate disease exacerbation as long as the patients still have practically normal functions of kidneys. However, the critical patients of kidney disease need long-term therapy of hemodialysis to maintain their life. The hemodialysis therapy normally causes discomfort to patients and incurs economic hardship.

Edible lactic acid bacteria are usually used to improve health of intestines. Please refer to Guidelines for the evaluation of probiotics in food; Report of joint FAO/WHO working group on drafting guidelines for the evaluation of probiotics in food; London Ontario, Canada April 30 and May 1, 2002: 1-7. It is found now: the efficacy of lactic acid bacteria to stabilize the flora in intestines may also improve chronic kidney disease. It is the specificity of a strain but not the whole species of lactic acid bacteria that can favor human health. The strains having special effects on human health are called probiotics. However, none of specific strains able to improve kidney disease has been verified so far. Thus, it has been a target of the related fields to develop probiotics able to improve kidney disease.

SUMMARY OF THE INVENTION

The present invention provides a pharmaceutic composition and a food composition both with strains of lactic acid bacteria for improving kidney disease and inhibiting inflammation, which can lower the level of blood urine nitrogen (BUN), serum creatinine (CRE) and urine albumen (Urine ALB), improve renal fibrosis, inhibit renal inflammation, and decelerate kidney disease exacerbation.

In one embodiment, the present invention provides a *lactobacillus* strain-containing pharmaceutic composition for improving kidney disease and inhibiting inflammation, which comprises an isolated lactic acid bacteria strain and a pharmaceutically-acceptable excipient or diluent. The lactic acid bacteria strain is at least one selected from a group consisting of *Bifidobacterium longum* subsp. *infantis* having a strain number BLI-02 and an accession number CGMCC No. 15212, *Lactobacillus acidophilus* having a strain number TYCA06 and an accession number CGMCC No. 15210, *Bifidobacterium bifidum* having a strain number VDD088 and an accession number CGMCC No. 15211, and combinations thereof. The abovementioned strains have physiological activity for improving kidney disease and inhibiting inflammation.

In another embodiment, the present invention provides a *lactobacillus* strain-containing food composition for improving kidney disease and inhibiting inflammation, which comprises an isolated lactic acid bacteria strain and a physiologically-acceptable excipient or diluent. The lactic acid bacteria strain is at least one selected from a group consisting of *Bifidobacterium longum* subsp. *infantis* having a strain number BLI-02 and an accession number CGMCC No. 15212, *Lactobacillus acidophilus* having a strain number TYCA06 and an accession number CGMCC No. 15210, *Bifidobacterium bifidum* having a strain number VDD088 and an accession number CGMCC No. 15211, and combinations thereof. The abovementioned strains have physiological activity for improving kidney disease and inhibiting inflammation.

In yet another embodiment, the present invention provides a use of a composition with strains of lactic acid bacteria for improving kidney disease and inhibiting inflammation comprising administering to a subject the composition, wherein the composition comprises an isolated lactic acid bacteria strain and a pharmaceutically-acceptable or physiologically-acceptable excipient or diluent. The lactic acid bacteria strain is at least one selected from a group consisting of *Bifidobacterium longum* subsp. *infantis* having a strain number BLI-02 and an accession number CGMCC No. 15212, *Lactobacillus acidophilus* having a strain number TYCA06 and an accession number CGMCC No. 15210, *Bifidobacterium bifidum* having a strain number VDD088 and an accession number CGMCC No. 15211, and combinations thereof. The abovementioned strains have physiological activity for improving kidney disease and inhibiting inflammation.

Below, embodiments are described in detail in cooperation with the attached drawings to make easily understood the objectives, technical contents, characteristics and accomplishments of the present invention.

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENTS

The present invention will be described in detail with embodiments and attached drawings below. However, these embodiments are only to exemplify the present invention but not to limit the scope of the present invention. In addition to the embodiments described in the specification, the present invention also applies to other embodiments. Further, any modification, variation, or substitution, which can be easily made by the persons skilled in that art according to the embodiment of the present invention, is to be also included within the scope of the present invention, which is based on the claims stated below. Although many special details are provided herein to make the readers more fully understand the present invention, the present invention can still be practiced under a condition that these special details are partially or completely omitted. Besides, the elements or steps, which are well known by the persons skilled in the art, are not described herein lest the present invention be limited unnecessarily. Similar or identical elements are denoted with similar or identical symbols in the drawings. It should be noted: the drawings are only to depict the present invention schematically but not to show the real dimensions or quantities of the present invention. Besides, matterless details are not necessarily depicted in the drawings to achieve conciseness of the drawings.

The freeze-dried cultures of the strains of lactic acid bacteria mentioned in the specification are preserved in China General Microbiological Culture Collection Center (CGMCC, address: Institute of Microbiology, Chinese Academy of Sciences, Datun Road, Chaoyang District, Beijing 100101, China). The details thereof are listed in Table.1.

TABLE 1

Data of preserved Strains of Lactic Acid Bacteria

| Strain | Specie | Deposition No. | Deposition Date |
| --- | --- | --- | --- |
| BLI-02 | *Bifidobacterium longum* subsp. *infantis* | CGMCC No. 15212 | Jan. 15, 2018 |
| TYCA06 | *Lactobacillus acidophilus* | CGMCC No. 15210 | Jan. 15, 2018 |
| VDD088 | *Bifidobacterium bifidum* | CGMCC No. 15211 | Jan. 15, 2018 |

In one embodiment, the present invention provides a pharmaceutical composition with strains of lactic acid bacteria for improving kidney disease and inhibiting inflammation, which comprises an isolated lactic acid bacteria strain and a pharmaceutically-acceptable excipient or diluent. The lactic acid bacteria strain is at least one selected from a group including BLI-02 strain, CGMCC No. 15212, *Bifidobacterium longum* subsp. *infantis*, TYCA06 strain, CGMCC No. 15210, *Lactobacillus acidophilus*, VDD088 strain, CGMCC No. 15211, *Bifidobacterium bifidum*, and combinations thereof. Each of the lactic acid bacteria strains may be an active one or an inactivated one. The number of the lactic acid bacteria strains ranges from $10^6$ to $10^{10}$ CFU (Colony-Forming Unit). Preferably, the number of the lactic acid bacteria strains ranges from $10^7$ to $10^9$ CFU.

In another embodiment, the present invention provides a food composition with strains of lactic acid bacteria for improving kidney disease and inhibiting inflammation, which comprises an isolated lactic acid bacteria strain and a physiologically-acceptable excipient or diluent. The lactic acid bacteria strain is at least one selected from a group including BLI-02 strain, CGMCC No. 15212, *Bifidobacterium longum* subsp. *infantis*, TYCA06 strain, CGMCC No. 15210, *Lactobacillus acidophilus*, VDD088 strain, CGMCC No. 15211, *Bifidobacterium bifidum*, and combinations thereof. Each of the lactic acid bacteria strains may be an active one or an inactivated one. Each of the lactic acid bacteria strains may be an active one or an inactivated one. The number of the lactic acid bacteria strains ranges from $10^6$ to $10^{10}$ CFU (Colony-Forming Unit).

In the embodiment of the food composition, the physiologically-acceptable excipient/diluent is a food. The food may be but is not limited to be dairy food, tea, coffee, or a combination thereof. The dairy food may be fermented milk, yoghurt, cheese, or powdered milk.

In the embodiment of the pharmaceutic composition, the pharmaceutic composition may be in form of a tablet, a capsule, a solution, or a powder. Below, several embodiments are used to verify the effects of the pharmaceutic composition and food composition both with strains of lactic acid bacteria of the present invention on improving kidney disease and inhibiting inflammation.

The taxonomic characteristics of the strains are identified with the 16S rDNA sequencing analysis and the API bacterial identification system. The morphologies and general properties of the strains are listed in Table.2.

TABLE. 2 morphologies and general properties of strains of lactic acid bacteria

| Strain | Morphology and characteristics |
| --- | --- |
| BLI-02 | 1. While cultured in the MRS medium, the body thereof has a shape of a short rod, and the ends of the body are oval-shaped. They often appear in single bodies or in pairs of short chains.<br>2. They are gram-positive bacilli, unlikely to generate spores, free of catalase, oxidase and motility, able to grow in aerobic and anaerobic environments, most suitable to grow at a temperature of 37 ± 1° C. They belong to a facultative heterofermentative strains and do not generate gas in glucose metabolism. |
| TYCA06 | 1. While cultured in the MRS medium, the body thereof has a shape of a middle-size rod, and the ends of the body are round-shaped. They often appear in single bodies or short chains.<br>2. They are gram-positive bacilli, unlikely to generate spores, free of catalase, oxidase and motility, able to grow in aerobic and anaerobic environments, most suitable to grow at a temperature of 37 ± 1° C . They belong to a facultative heterofermentative strains and do not generate gas in glucose metabolism. |
| VDD088 | 1. While cultured in the MRS medium, the body thereof has a shape of a short or middle-size rod, and the ends of the body are oval-shaped. They often appear in single bodies or in pairs of short chains.<br>2. They are gram-positive bacilli, unlikely to generate spores, free of catalase, oxidase and motility, able to grow in aerobic and anaerobic environments, most suitable to grow at a temperature of 37 ± 1° C. They belong to a facultative heterofermentative strains and do not generate gas in glucose metabolism. |

In order to verify the effects of the strains on improving kidney disease and inhibiting inflammation, adenine is used to induce nephritis of mice for experiments. The steps of experiments include 1. Provide 6-8 week-old SPF (Specific-Pathogen-Free) C57BL/6 male mice, and divide them into four groups as shown in Table.3;

TABLE 3

| Group | Feed | | Lactic acid bacteria strains of the present invention |
|---|---|---|---|
| | Powdered Feed | 0.2 wt % Adenine | (200 μL by gavage) |
| Control group (N) | + | − | − |
| Comparison group (A) | + | + | − |
| Embodiment 1 (L) | + | + | $10^7$ CFU |
| Embodiment 2 (H) | + | + | $10^9$ CFU |

The lactic acid bacteria strain is selected from a group including BLI-02 strain, CGMCC No. 15212, *Bifidobacterium longum* subsp. *infantis*, TYCA06 strain, CGMCC No. 15210, *Lactobacillus acidophilus*, VDD088 strain, CGMCC No. 15211, *Bifidobacterium bifidum*, and combinations thereof.

2. Weigh the mice before experiments; weigh the mice and the feed intake thereof each week during experiments.

3. Sacrifice the four groups of mice 6 weeks later; measure the blood pressure of the mice and collect the blood samples and urine samples of the mice one day before sacrifice; take out the kidneys of the mice to evaluate the tissues of the kidneys.

4. Express the experimental data with mean±SEM; use Student's t-test to inspect whether there is any statistically significant result; if the p value is smaller than 0.05, it is statistically significant, wherein *$p<0.05$; $p<0.01$; *$p<0.001$.

It is preferred: the ratio of the numbers of the lactic acid bacteria in the strains is TYCA06:BLI02:VDD88=3:4:3. However, the present invention is not limited by the ratio. In other embodiments, the ratio of the numbers of the lactic acid bacteria in the strains may be TYCA06:BLI02:VDD88=10:0:0, or TYCA06:BLI02:VDD88=0:10:0, or TYCA06:BLI02:VDD88=0:0:10.

Figure 1:
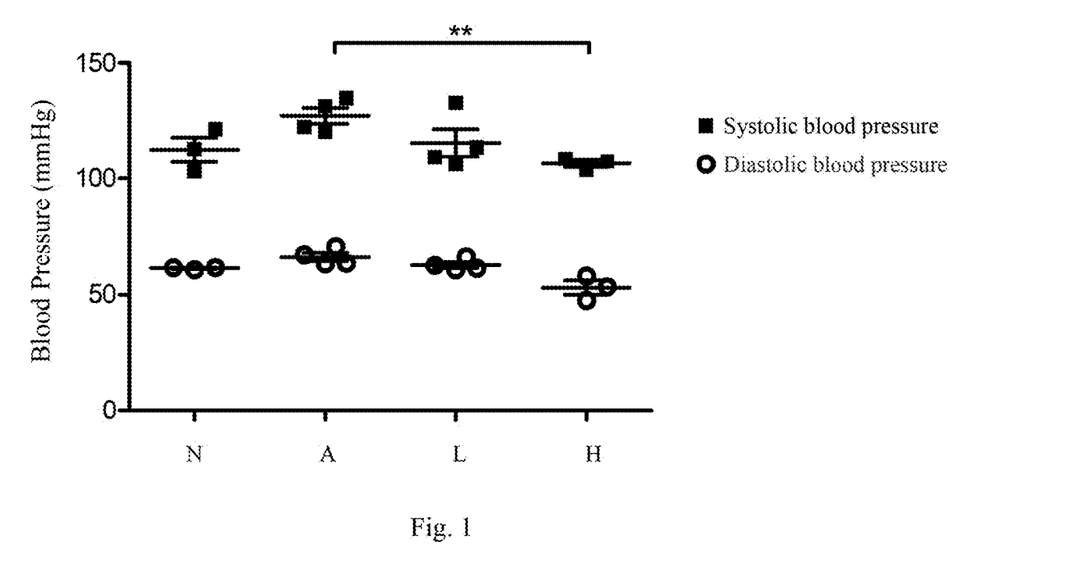
FIG. 1 shows the blood pressures of the mice in all the groups.
Figure 2:
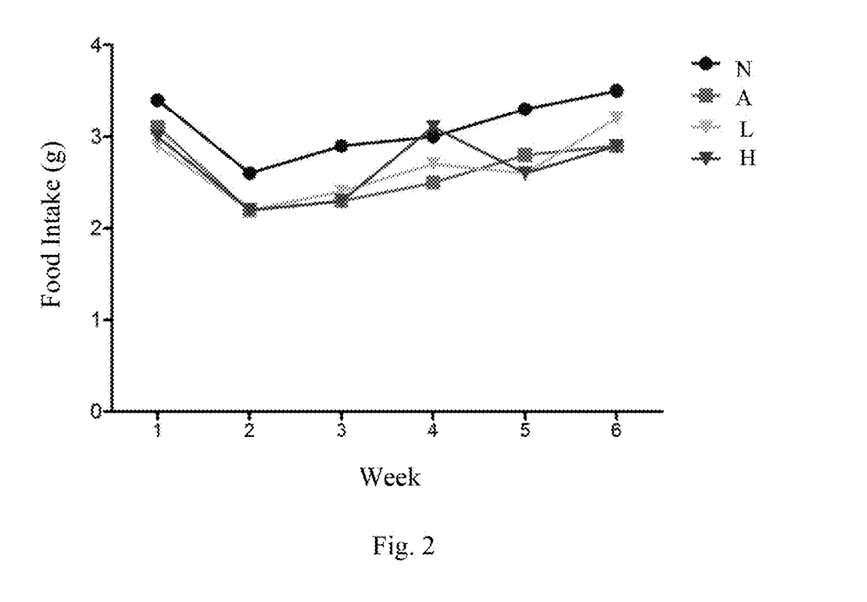
FIG. 2 shows the food intakes of the mice in all the groups.

The experimental results will be explained with the drawings below. Refer to FIG. 1 for a comparison of the blood pressures of the mice. In general, obstruction of kidneys will lead to increase of blood pressure. Therefore, blood pressure can be used to evaluate improvement of kidney disease. It is observed in FIG. 1: the blood pressure of the comparison group is significantly higher than the blood pressure of the control group. It indicates that feeding 0.2% adenine indeed increases blood pressure. However, the blood pressure of the mice has a tendency to decrease in the groups fed with the lactic acid bacteria strains of the present invention, especially in the group fed with a high dosage. It shows that the obstruction of the kidneys of the mice in the groups fed with the lactic acid bacteria strains is indeed relieved and the effect is dose-dependent. FIG. 2 shows that the weekly intakes are substantially invariant for all the groups of mice.

Figure 3:
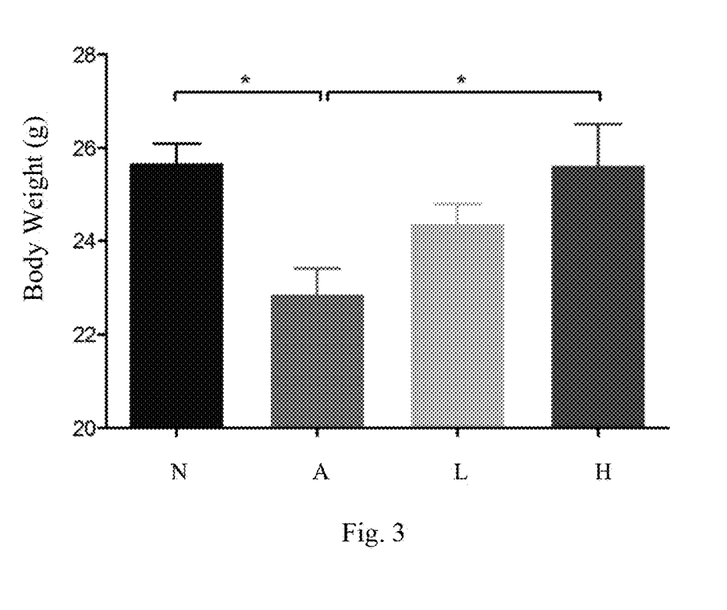
FIG. 3 shows the body weights of the mice in all the groups.

FIG. 3 shows the comparison of the body weights of all the groups of mice. In the groups fed with 0.2% adenine and the lactic acid bacteria strains of the present invention (Embodiment I and Embodiment II), the body weights thereof all increase. The body weights of the mice in the group fed with a higher dosage of the lactic acid bacteria strains of the present invention (Embodiment II) are in the same range as the body weights of the mice in the control group. As the metabolism is abnormal in the individuals suffering kidney disease, the body weights thereof are likely to decrease. It is found in this embodiment: the body weights of the mice fed with the lactic acid bacteria strains of the present invention are likely to be restored, and the effect is dose-dependent. It indicates that the lactic acid bacteria strains of the present invention can recover the health of kidneys obviously.

Next, the kidney functions of all the groups are evaluated. In general, the evaluation of the kidney function includes measuring the sizes and weights of the kidneys and detecting BUN, creatinine, and urinary protein.

Figure 4A:
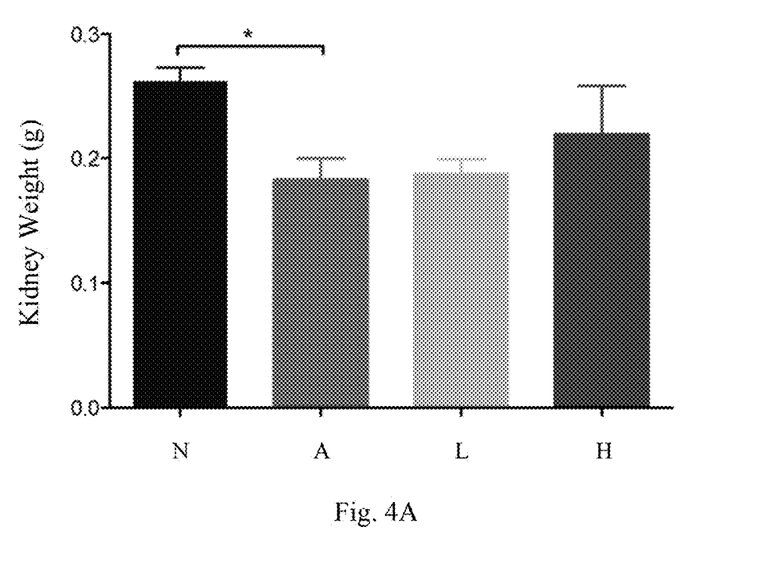
FIG. 4A shows the weights of the kidneys of the mice in all the groups.
Figure 4B:
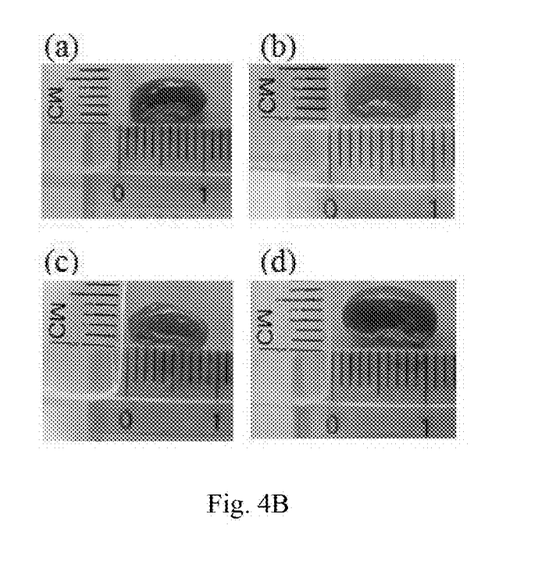
FIG. 4B shows the appearances of the kidneys of the mice in all the groups.

Refer to FIG. 4A. Compared with the kidney weights of the mice in the comparison group, the kidney weights of the mice in Embodiment II has a tendency to increase. The surface smoothness and shape integrity is used to estimate the states of the kidneys. Refer to FIG. 4B, wherein the kidney of the mouse in the control group is shown in Part (a); the kidney of the mouse in the comparison group is shown in Part (b); the kidney of the mouse in Embodiment I is shown in Part (c); the kidney of the mouse in Embodiment II is shown in Part (d). It is found: the kidney of the mouse in the comparison group is less smooth and slightly contracted. The kidneys of the mice in Embodiment I and Embodiment II have higher smoothness and integrity, and no big discrepancy exists between the control group and Embodiment I/Embodiment II. Therefore, the lactic acid bacteria strains of the present invention favor repair of kidneys.

Figure 5A:
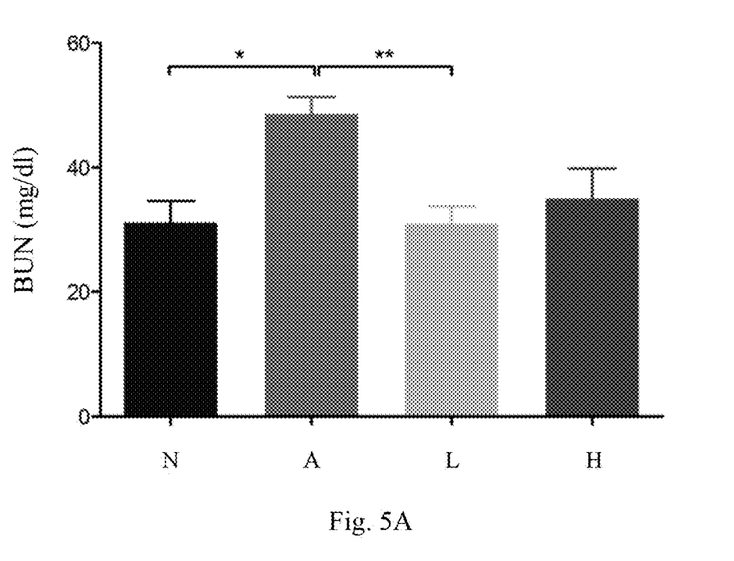
FIG. 5A and FIG. 5B show the results of the biochemical inspections of the plasma of the mice in all the groups.
Figure 5B:
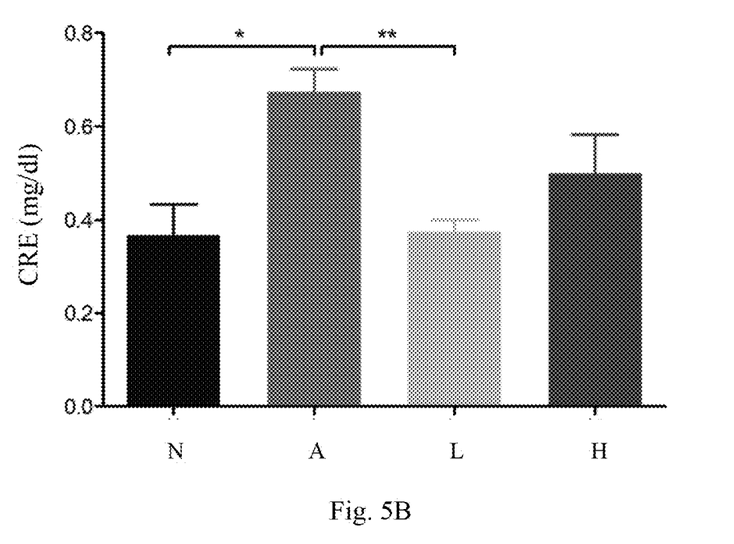

Refer to FIG. 5A and FIG. 5B for the results of the BUN analysis and creatinine analysis. A dry-type biochemical analyzer FUJI DRI-CHEM 4000i is used to undertake the analyses. The levels of BUN and creatinine of the mice in the comparison group is significantly higher than those of the control group. The levels of BUN and creatinine of the mice in Embodiment I and Embodiment II have a tendency to decrease, and the levels are decreased to the levels of the control group. It indicates that the lactic acid bacteria strains of the present invention favor repair of kidneys.

Figure 6:
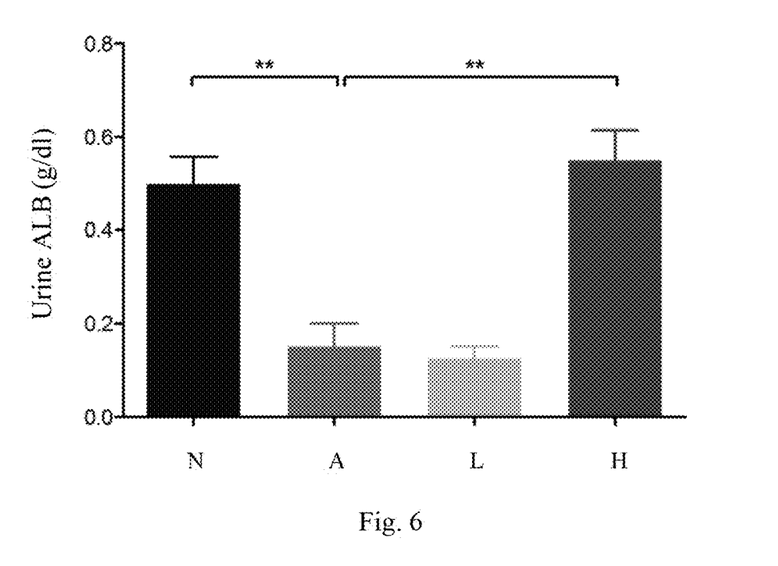
FIG. 6 shows the results of the urinary protein analyses of the mice in all the groups.

For analyzing urinary protein, 10 μl urine sample and 10 μl standard solution are added to each well of a 96-well plate. Next, 200 μl diluted Bio-rad dye is added to each well. Next, the 96-well plate is oscillated for 5 minutes. Then, absorption of 595 nm light is measured. The standard samples, the standard curve of light absorption, and a regression method are used to acquire an equation. The equation and the interpolation method are used to calculate the concentration of albumen in urine. In general, the function of renal dialysis of the patients suffering kidney disease degrades, and the albumen in the urine is likely to increase. In the comparison group, Embodiment I, and Embodiment II, the mice are induced to have an acute nephritis, i.e. an obstructive renal disease. The obstructive renal disease would contrarily decrease albumen in urine. Refer to FIG. 6. The concentration of albumen in the urine of the mice in Embodiment II is obviously restored to the same as that in the control group. It shows that the lactic acid bacteria strains of the present invention can improve the nephritis-induced abnormal urine albumen concentration, and the effect is dose-dependent.

Figure 7:
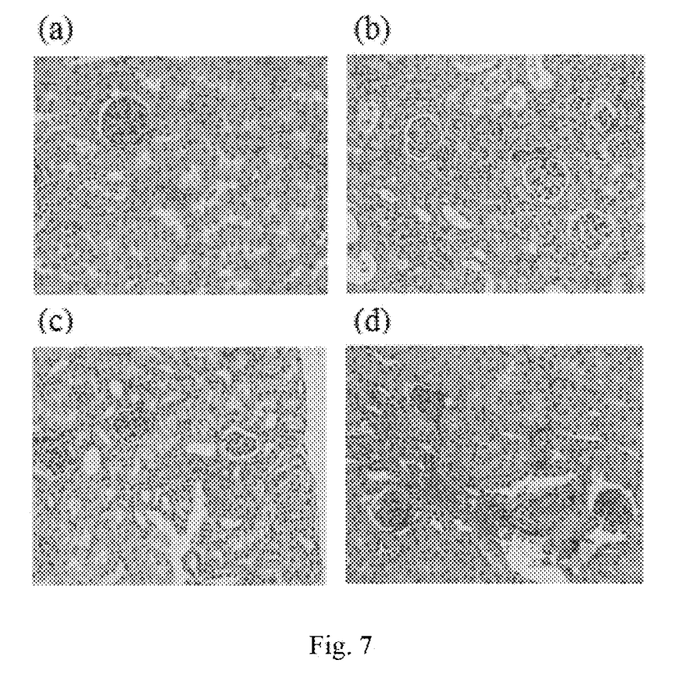
FIG. 7 and FIG. 8 show the stained kidney tissue sections of the mice in all the groups.

In medicine, chronic kidney disease is normally caused by long-term inflammation, which may be due to infection, immune complex disease, inflammatory reaction, etc. and may damage the structure and function of kidneys. If the inflammation of kidneys can be repressed, the symptoms of kidney disease should be relieved, and the progression of kidney disease should be inhibited. Below are described the effects of the pharmaceutic composition of the present invention on inflammation. Refer to FIG. 7 for the stained tissue sections (by H&M stain or MT stain) of the kidneys of all the groups of mice, wherein 2 mm thick left kidney tissue sections of the mice are fixed in neutral formalin and stained with hematoxylin and eosin stain (H&M stain). In FIG. 7, Part (a) shows the stained kidney tissue section of the mouse of the control group; Part (b) shows the stained kidney tissue section of the mouse of the comparison group; Part (c) shows the stained kidney tissue section of the mouse of Embodiment I; Part (d) shows the stained kidney tissue section of the mouse of Embodiment II. It is observed in FIG. 7: the kidney of the mouse in the comparison group is infiltrated by a great amount of immune cells; the levels of immune cell infiltration of the kidneys of the mice in Embodiment I and Embodiment II are similar to that in the control group. In general, inflammatory reaction is a protective immune response of a vivo tissue to the harm caused by an external or internal factor. The more serious the inflammatory reaction, the more obvious the immune cell infiltration. It is seen in FIG. 7: the immune cell infiltration in Embodiments I and II is less than that in the comparison group. It indicates that inflammation is improved or inhibited in Embodiments I and II.

Figure 8:
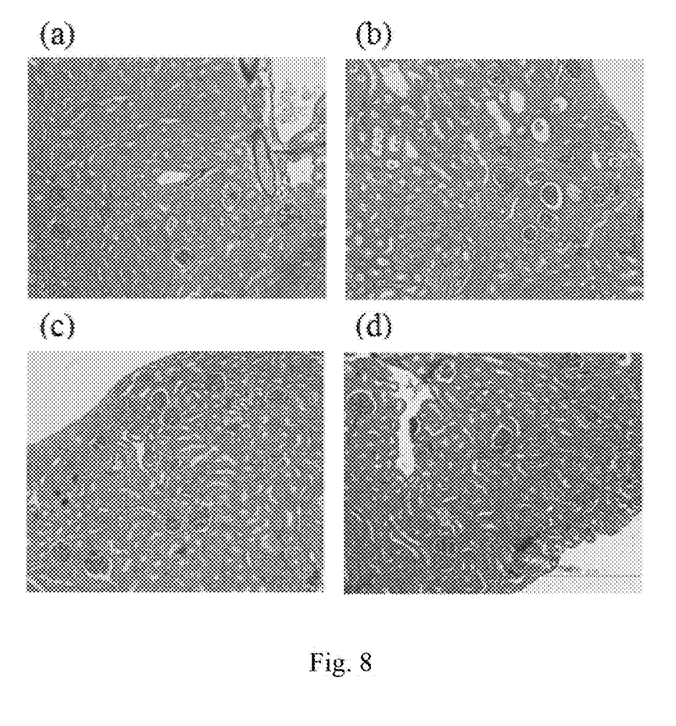

While the kidney inflames persistently, renal fibrosis will take place in the long run. The tissue sections of the mice in all the groups are stained with the MT stain method to observe the renal fibrosis thereof. Refer to FIG. 8. In FIG. 8, Part (a) shows the stained kidney tissue section of the mouse of the control group; Part (b) shows the stained kidney tissue section of the mouse of the comparison group; Part (c) shows the stained kidney tissue section of the mouse of Embodiment I; Part (d) shows the stained kidney tissue section of the mouse of Embodiment II. It is observed in FIG. 8: the renal fibrosis of the mouse in the comparison group is more serious; the renal fibrosis of the mice in Embodiments I and II is gradually similar to that in the control group; a big discrepancy of renal fibrosis exists between the comparison group and Embodiment I/II, especially between the comparison group and Embodiment II, which is fed with a high dosage of lactic acid bacteria strains.

In summary, the pharmaceutic composition and the food composition both with strains of lactic acid bacteria of the present invention are able to improve kidney disease and inhibit inflammation. The present invention can lower blood urine nitrogen (BUN), serum creatinine (CRE) and urine albumen (Urine ALB) for individuals suffering kidney disease, improve renal fibrosis, inhibit renal inflammation, and decelerate kidney disease exacerbation.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the appended claims.

Biological Material Preservation

[1] China General Microbiological Culture Collection Center, Jan. 15, 2018, CGMCC No. 15212;
[2] China General Microbiological Culture Collection Center, Jan. 15, 2018, CGMCC No. 15210;
[3] China General Microbiological Culture Collection Center, Jan. 15, 2018, CGMCC No. 15211.

What is claimed is:

1. A pharmaceutical composition in the form of a tablet, a capsule or a powder with strains of lactic acid bacteria for improving kidney disease and inhibiting inflammation, comprising:

a combination of isolated lactic acid bacteria including *Bifidobacterium longum* subsp. *infantis* having a strain number BLI-02 and an accession number CGMCC No. 15212, *Lactobacillus acidophilus* having a strain number TYCA06 and an accession number CGMCC No. 15210, and *Bifidobacterium bifidum* having a strain number VDD088 and an accession number CGMCC No. 15211, wherein the abovementioned strains have physiological activity for improving kidney disease and inhibiting inflammation and are preserved in China General Microbiological Culture Collection Center (CGMCC); and a pharmaceutically acceptable excipient or diluent.

2. The pharmaceutical composition according to claim 1, wherein the lactic acid bacteria are active.

3. The pharmaceutical composition according to claim 1, wherein the lactic acid bacteria are deactivated.

4. The pharmaceutical composition according to claim 1, wherein each lactic acid bacteria strain is at a concentration from $10^6$ to $10^{10}$ CFU (Colony-Forming Unit).

5. A food composition with strains of lactic acid bacteria for improving kidney disease and inhibiting inflammation, comprising:

a combination of isolated lactic acid bacteria including *Bifidobacterium longum* subsp. *infantis* having a strain number BLI-02 and an accession number CGMCC No. 15212, *Lactobacillus acidophilus* having a strain number TYCA06 and an accession number CGMCC No. 15210, and *Bifidobacterium bifidum* having a strain number VDD088 and an accession number CGMCC No. 15211, wherein the abovementioned strains have physiological activity for improving kidney disease and inhibiting inflammation and are preserved in China General Microbiological Culture Collection Center (CGMCC); and a physiologically acceptable excipient or diluent comprising fermented milk, yogurt, cheese, powdered milk, tea, coffee, or a combination thereof.

6. The food composition according to claim 5, wherein the lactic acid bacteria are active.

7. The food composition according to claim 5, wherein the lactic acid bacteria are deactivated.

8. The food composition according to claim 5, wherein each lactic acid bacteria strain is at a concentration from $10^6$ to $10^{10}$ CFU (Colony-Forming Unit).

9. A method for improving kidney disease and inhibiting inflammation, comprising administering the composition according to claim 1 to a patient.

10. The method according to claim 9, wherein the lactic acid bacteria are active.

11. The method according to claim 9, wherein the lactic acid bacteria are deactivated.

12. The method according to claim 9, wherein each lactic acid bacteria strain is at a concentration from $10^6$ to $10^{10}$ CFU (Colony-Forming Unit).

13. A method for improving kidney disease and inhibiting inflammation, comprising administering the composition according to claim 5 to a patient.

14. The method according to claim 13, wherein the lactic acid bacteria are active.

15. The method according to claim 13, wherein the lactic acid bacteria are deactivated.

16. The method according to claim 13, wherein each lactic acid bacteria strain is at a concentration from $10^6$ to $10^{10}$ CFU (Colony-Forming Unit).

* * * * *